United States Patent
Khouri (12) 
(10) Patent No.: US 6,478,656 B1
(45) Date of Patent: Nov. 12, 2002

(54) METHOD AND APPARATUS FOR EXPANDING SOFT TISSUE WITH SHAPE MEMORY ALLOYS

(75) Inventor: Roger K. Khouri, Key Biscayne, FL (US)

(73) Assignee: Brava, LLC, Coconut Grove, FL (US)

( * ) Notice: Subject to any disclaimer, the term of this patent is extended or adjusted under 35 U.S.C. 154(b) by 0 days.

(21) Appl. No.: 09/203,832

(22) Filed: Dec. 1, 1998

(51) Int. Cl.[7] ................................................. A41C 3/00
(52) U.S. Cl. ............................... 450/39; 450/1; 600/38
(58) Field of Search ................................ 450/1, 40, 39, 450/41–44, 65–70, 74–81; 600/38–41

(56) References Cited

U.S. PATENT DOCUMENTS

| | | |
|---|---|---|
| 532,236 A | 1/1895 | Hardesty |
| 936,434 A | 10/1909 | Eganhouse |
| 1,021,688 A | 3/1912 | Jeune |
| 1,312,619 A | 8/1919 | D'Orsay |
| 1,472,234 A | 10/1923 | Thomas |
| 2,012,755 A | 7/1935 | Demuth |
| 2,616,417 A | 11/1952 | Holbrook |
| 2,817,333 A | 12/1957 | Cole |
| 3,174,851 A | 3/1965 | Buehler et al. |
| 3,382,867 A | 5/1968 | Reaves |
| 3,568,675 A | 3/1971 | Harvey |
| 3,631,853 A | 1/1972 | Burdette, Jr. |
| 3,785,369 A | 1/1974 | Tallent |
| 3,859,989 A | 1/1975 | Spielberg |
| 3,874,387 A | 4/1975 | Barbieri |
| 3,908,662 A | 9/1975 | Razgulov et al. |
| 3,939,827 A | 2/1976 | Brunstetter |
| 4,029,088 A | 6/1977 | Wu |
| 4,175,554 A | 11/1979 | Gerow |
| 4,368,883 A | 1/1983 | Tiktin |
| 4,633,865 A | 1/1987 | Hengstberger et al. |
| 4,653,484 A | 3/1987 | Cannon |
| 4,706,661 A | 11/1987 | Barrett |
| 4,718,411 A | 1/1988 | Stewart |
| 4,770,176 A | 9/1988 | McGreevy et al. |
| 4,774,091 A | 9/1988 | Yamahira et al. |

(List continued on next page.)

FOREIGN PATENT DOCUMENTS

| | | |
|---|---|---|
| DE | 3019589 A1 | 8/1982 |
| SU | 1319853 | 6/1987 |
| WO | WO91/17727 | 11/1991 |
| WO | WO93/09727 | 5/1993 |

OTHER PUBLICATIONS

Francis, A.J. and Marks, R. Skin Stretching and Epidermopoiesis, Br. J. exp. Path. 58:35, 1977.

Squier, C.A. The Stretching of Mouse Skin in Vivo: Effects on Epidermal Proliferation and Thickness. The Journal of Investigative Dermatology 74:68, 1980.

(List continued on next page.)

Primary Examiner—Gloria M. Hale
(74) Attorney, Agent, or Firm—Thompson Coburn LLP (57) ABSTRACT

A soft tissue expander comprises a dome having a layer of memory material which transitions from a first, shallower, malleable configuration to a second, deeper configuration in response to its being heated to its transition temperature which is set at human body surface temperature. The second, deeper configuration is first "set" in the memory of the memory material so that the dome returns to it upon being heated by the body temperature of the patient. The memory material may be any one of the shape memory alloys, or plastic materials. The interior of the dome is adhered to the skin of the soft tissue to be expanded, such as through sticky layer of gel or surface tension provided by a thin layer of fluid. In one embodiment, a bra has a pair of domes for covering a patient's breasts and which applies a tensile force thereon to thereby increase their size.

27 Claims, 4 Drawing Sheets

U.S. PATENT DOCUMENTS

| | | | |
|---|---|---|---|
| 4,834,110 A | 5/1989 | Richard |
| 4,856,498 A | 8/1989 | Osbon |
| 4,856,499 A | 8/1989 | Kelly |
| 4,930,674 A | 6/1990 | Barak |
| 4,995,381 A | 2/1991 | Marmar et al. |
| 5,059,211 A | 10/1991 | Stack et al. |
| 5,141,516 A | 8/1992 | Detweiler |
| 5,197,978 A | 3/1993 | Hess |
| 5,234,401 A | 8/1993 | Yamanaka |
| 5,254,113 A | 10/1993 | Wilk |
| 5,273,900 A | 12/1993 | Boyce |
| 5,274,074 A | 12/1993 | Tang et al. |
| 5,276,015 A | 1/1994 | Khouri et al. |
| 5,292,802 A | 3/1994 | Rhee et al. |
| 5,308,889 A | 5/1994 | Rhee et al. |
| 5,312,333 A | 5/1994 | Churinetz et al. |
| 5,314,472 A | 5/1994 | Fontaine |
| 5,336,158 A | 8/1994 | Huggins et al. |
| 5,344,396 A | 9/1994 | Clark, Jr. |
| 5,370,685 A | 12/1994 | Stevens |
| 5,464,450 A | 11/1995 | Busscemi et al. |
| 5,468,220 A | 11/1995 | Sucher |
| 5,476,091 A | 12/1995 | Johnson |
| 5,476,478 A | 12/1995 | Jackson |
| 5,533,499 A | 7/1996 | Johnson |
| 5,536,233 A | 7/1996 | Khouri |
| 5,636,643 A | 6/1997 | Argenta et al. |
| 5,645,081 A | 7/1997 | Argenta et al. |
| 5,653,744 A | 8/1997 | Khouri |
| 5,662,583 A | 9/1997 | Khouri |
| 5,676,634 A | 10/1997 | Khouri |
| 5,695,445 A | 12/1997 | Khouri |
| 5,701,917 A | 12/1997 | Khouri |
| 5,723,115 A | 3/1998 | Serrero |
| 6,042,537 A | 3/2000 | Kaiser |
| 6,083,912 A | 7/2000 | Khouri |
| 6,086,866 A | 7/2000 | Khouri |

OTHER PUBLICATIONS

Austad, E.D., Thomas, S.B., and Pasyk, K. Tissue Expansion: Dividend or Loan? Plastic and Reconstructive Surgery 78:63, 1986.

Pasyk, K.A., Argenta, L.C., and Austad, E.D. Histopathology of Human Expanded Tissue. Clinics in Plastic Surgery 14:435, 1987.

Olenius, M., Dalsgaard, C.J. and Wickman, M. Mitotic Activity in Expanded Human Skin. Plastic and Reconstructive Surgery 91:213, 1993.

De Witt, M.T., Handley, C.J. Oakes, B.W., and Lowther D.A. In Vitro Response of Chondrocytes to Mechanical Loading. The Effect of Short Term Mechanical Tension. Connective Tissue Research 12:97, 1984.

Carter, D.R., Fyhrie, D.P. and Whalen, R.T. Trabecular Bone Density and Loading History: Regulation of Connective Tissue Biology by Mechanical Energy. J. Biomechanics 20:785, 1987.

Carter, D.R. Mechanical Loading History and Skeletal Biology. J. Biomechanics 20:1095, 1987.

Skoulis, T.G., Lovice, D., von Fricken, K., and Terzis, J.K. Nerve Expansion The Optimal Answer for the Short Nerve Gap. Behavioral Analysis. Clinical Orthopaedics and Related Research 314:84, 1995.

Wood, R.J., Adson, M.H., VanBeek, A.L., Peltier, G.L., Zubkoff, M.M., and Bubrick, M.P., Controlled Expansion of Peripheral Nerves: Comparison of Nerve Grafting and Nerve Expansion/Repair for Canine Sciatic Nerve Defects. The Journal of Trauma 31:686, 1991.

Manders, E.K., Saggers, G.C., Diaz–Alonzo, P., Finn, L., Sipio, J.C. Glumac, T., Au, V.K. Wong, R.K.M., and Mottaleb, M. Elongation of Peripheral Nerve and Viscera Containing Smooth Muscle. Clin. Plast. Surg. 14:551, 1987.

Stark, G.B., Hong, C., and Futrell, J.W. Rapid Elongation of Arteries and Veins in Rats with a Tissue Expander. Plastic and Reconstructive Surgery 80:570, 1987.

Wilson, E., Mai, Q., Sudhir, K., Weiss, R.H. and Ives, H.E. Mechanical Strain Induces Growth of Vascular Smooth Muscle Cells via Autocrine Action of PDGF. Journal of Cell Biology 123:741, 1993.

Sumpio, B.E., Banes, A.J., Link, W.G., and Johnson, G., Jr. Enhanced Collagen Production by Smooth Muscle Cells During Repetitive Mechanical Stretching. Arch. Surg. 123:1233, 1988.

Vandenburgh, H. and Kaufman, S. In vitro Model for Stretch–Induced Hypertrophy of Skeletal Muscle. Science 203:265, 1979.

Kim, K.H., Hong, C., and Futrell, J.W. Histomorphologic Changes in Expanded Skeletal Muscle in Rats. Plastic and Reconstructive Surgery 92:710, 1993.

Vandenburgh, H.H. Motion into mass: how does tension stimulate muscle growth? Medicine and Science in Sports and Exercise 19:S142, 1987.

Alway, S.E., Winchester, P.K., Davis, M.E., and Gonyea, W. Regionalized adaptations and muscle fiber proliferation in stretch–induced enlargement. Journal of Applied Physiology 66:771, 1989.

Finn, L.S., Saggers, G., Manders, E.K., and Rose, R.C. Soft Tissue Expansion to Elongate the Small Bowel. Surgical Forum 39:604, 1988.

Narayan, D., Castro, A., Jackson, I.T., and Herschman, B. Tissue expanders in the gut: a histological and angiographic study. J.R. Coll. Surg. Edinb. 37:402, 1992.

Bianchi, A. Intestinal Loop Lenghtening A Technique for Increasing Small Intestinal Length. Journal of Pediatric Surgery 15:145, 1980.

Kimura, K. and Soper, R.T. A New Bowel Elongation Technique for the Short–Bowel Syndrome Using the Isolated Bowel Segment Lowa Models. Journal of Pediatric Surgery 28:792, 1993.

Rannels, D.E. Role of physical forces in compensatory growth of the lung. American Journal of Physiology 257:L179, 1989.

Russo, L.A., Rannels, S.R., Laslow, K.S., and Rannels, D.E. Stretch–related changes in lung cAMP after partial pneumonectomy. American Journal of Physiology: Endocrinology and Metabolism 20:E261, 1989.

Curtis, A.S.G. and Seehar, G.M. The control of cell division by tension or diffusion. Nature 274:52, 1978.

Brunette, D.M. Mechanical Stretching Increases the Number of Epithelial Cells Synthesizing DNA in Culture. J. Cell. Sci. 69:35, 1984.

Jain, M.K., Berg, R.A., and Tandon, G.P. Mechanical stress and cellular metabolism in living soft tissue composites. Biomaterials 11:465, 1990.

Rodriguez, E.K., Hoger, A., and McCulloch, A.D. Stress Dependent Finite Growth in Soft Elastic Tissues. J. Biomechanics 27:455, 1994.

Folkman, J. and Moscona, A. Role of cell shape in growth control. Nature 273:345, 1978.

Urschel, J.D., Scott, P.G. and Williams, H.T.G. The effect of mechanical stress on soft and hard tissue repair; a review. British Journal of Plastic Surgery 41:182, 1988.

Ryan, T.J. Biochemical consequences of mechanical forces generated by distention and distortion. J. Am. Acad. Dermatol 21:115, 1989.

Watson, P.A. Function follows form: generation of intracellular signals by cell deformation. FASEB J. 5:2013, 1991.

Vandenburgh, H.H. Mechanical forces and their second messengers in stimulating cell growth in vitro. American Journal of Physiology 262:R350, 1992.

Takei, T., Mills, I., Katsuyuki, A., and Sumpio, B.E. Molecular Basis for Tissue Expansion: Clinical Implications for the Surgeon. Plastic and Reconstructive Surgery 101:247, 1998.

Ruoslahti, E. Stretching Is Good for a Cell. Science 276:1345, 1997.

Neumann, C.G. The Expansion of an Area of Skin by Progressive Distention of a Subcutaneous Balloon. Plastic and Reconstructive Surgery 19:124, 1957.

Radovan, C. Tissue Expansion in Soft Tissue Reconstruction. Plastic and Reconstructive Surgery 74:482, 1984.

Mackinnon, S.E. and Gruss, J.S. Soft tissue expanders in upper limb surgery. The Journal of Hand Surgery. 10A:749, 1985.

Argenta, L.C. Controlled tissue expansion in reconstructive surgery. British Journal of Plastic Surgery 37:520, 1984.

Manders, E.K., Schenden, M.J., Furrey, J.A., Hetzler, P.T., Davis, T.S. and Graham, W.P. Soft–Tissue Expansion: Concepts and Complications. Plastic and Reconstructive Surgery 74:493, 1984.

Mustoe, T.A., Bartell, T.H. and Garner, W.L. Physical, Biomechanical, Histologic, and Biochemical Effects of Rapid versus Conventional Tissue Expansion. Plastic and Reconstructive Surgery 83:687, 1989.

Marcus, J., Horan, D.B., and Robinson, J.K. Tissue expansion: past, present, and future. The Journal of the American Academy of Dermatology 23:813, 1990.

Johnson, T.M., Lowe, L., Brown, M.D., Sullivan, M.J., and Nelson, B.R. Histology and Physiology of Tissue Expansion. J. Dermatol Surg. Oncol. 19:1074, 1993.

Bennett, R.G. and Hirt, M. A History of Tissue Expansion: Concepts, Controversies, and Complications. J. Dermatol Surg. Oncol. 19:1066, 1993.

Becker, H. Breast Reconstruction Using an Inflatable Breast Implant with Detachable Reservoir. Plasic and. Reconstructive Surgery 73:678, 1984.

Chisolm, E.M., Marr, S., Macfie, J., Broughton, A.C. and Brennan, T.G. Post–mastectomy breast reconstruction using the inflatable tissue expander. Br. J. Surg. 73:817, 1986.

Slavin, S.A. and Colen, S.R. Sixty Consecutive Breast Reconstructions with the Inflatble Expander: A Critical Appraisal. Plastic and Reconstructive Surgery. 86:910, 1990.

McGeorge, D.D. The "Niplette": an instrument for the non–surgical correction of inverted nipples, British Journal of Plastic Surgery 47:46, 1994.

Herzenberg, J.E., Davis, J.R., Paley, D., and Bhave, A. Mechanical Distraction for Treatment of Severe Knee Flexion Contractures. Clinical Orthopaedics and Related Research 301:80, 1994.

Volkov, M.V. and Oganesian, O.V. Restoration of Function in the Knee and Elbow with a Hinge–Distractor Apparatus. The Journal of Bone and Joint Surgery 57A:591, 1975.

Mingli, Z., Dawei, W., and Lan, H. The Application of Skin External Expander to Postburn Advanced Scar Contracture. Plastic and Reconstructive Surgery 96:1600, 1995.

Cohen, B.H. and Cosmetto, A.J. The Suture Tension Adjustment Reel. J. Dermatol. Surg. Oncol. 18:112, 1992.

Ilizarov, G.A. The Tension–Stress Effect on the Genesis and Growth of Tissues: Part I The Influence of Stability of Fixation and Soft–Tissue Preservation. Clinical Orthopaedics and Related Research 238:249, 1989.

Ilizarov, G.A. The Tension–Stress Effect on the Genesis and Growth of Tissues: Part II The Influence of the Rate and Frequency of Distraction. Clinical Orthopaedics and Related Research 239:263, 1989.

Ilizarov, G.A. Clinical Application of the Tension–Stress Effect for Limb Lengthening. Clinical Orthopaedics and Related Research 250:8, 1990.

Coleman, S.S. and Scott, S.M. The Present Attitude Toward the Biology and Technology of Limb Lengthening. Clinical Orthopaedics and Related Research 264:76, 1991.

Paley, D., Rumley, T.O., and Kovelman, H. The Ilizarov Technique: A Method to Regenerate Bone and Soft Tissue. Advanced Plast Reconstr Surg 7:1, 1991.

Villa, A., Paley, D., Catagni, M.A., Bell, D., and Cattaneo, R. Lengthening of the Forearm by the Ilizarov Technique. Clinical Orthopaedics and Related Research 250:125, 1990.

Stricker, S.J. Ilizarov Lengthening of a Posttraumatic Below Elbow Amputation Stump. Clinical Orthopaedics and Related Research 306:124, 1994.

McCarthy, J.G., Schreiber, J., Karp, N., Thorne, C.H., and Grayson, B.H. Lengthening the Human Mandible by Gradual Distraction. Plastic and Reconstructive Surgery 89:1, 1992.

Polley, J.W. and Figueroa, A.A. Management of Severe Maxillary Deficiency in Childhood and Adolescence Through Distraction Osteogenesis With an External, Adjustable, Rigid Distraction Device. The Journal of Cranofacial Surgery 8:181, 1997.

Cohen, S.R., Burstein, F.D., Stewart, M.B., and Rathburn, M.A. Maxillary–Midface Distraction in Children with Cleft Lip and Palate: A Preliminary Report. Plastic and Reconstructive Surgery 99:1421, 1997.

Cohen, S.R., Rutrick, R.E., and Burstein, F.D. Distraction Osteogenesis of the Human Craniofacial Skeleton: Initial Experience with a New Distraction System. The Journal of Cranofacial Surgery 6:368, 1995.

Block, M.S., Cervini, D., Chang, A. and Gottsegen, G.B. Anterior Maxillary Advancement Using Tooth–Supported Distraction Osteogenesis. J. Oral Maxillofac. Surg. 53:561, 1995.

Sugihara, T., Kawashima, K., Igawa, H., Ohura, T., Yamamura, M., and Ohata, N. Mandibular lengthening by gradual distraction in humans. European Journal of Plastic Surgery 18:7, 1995.

Rachmiel, A., Potparic, Z., Jackson, I.T. et al. Midface advancement by gradual distraction. British Journal of Plastic Surgery 46:201, 1993.

Copy of *Enlargement Book,* ©1990 Topco Books.

Copy of *An Anthology Of Plastic Surgery,* edited by Harry Hayes, Jr., M.D., specifically Section 6 entitled "Quackery and Nostrums", Aspen Publishers, Inc., 1986, pp. 163–175.

Article entitled "The Tension–Stress Effect on the Genesis and Growth of Tissues—Part I. The Influence of Stability of Fixation and Soft–Tissue Preservation" by Gabriil A. Ilizarov. AM., M.D., Ph.D., from *Clinical Orthopaedics and Related Research*, from Section III, entitled "Basic Science And Pathology", No. 238, Jan. 1989, pp. 249–281.

Article entitled "The 'Niplette': an instrument for the non-surgical correction of inverted nipples" by D.D. McGeorge, from *British Journal Of Plastic Surgery* 1994, pp. 46–49.

Copy of *How To Enlarge Your Penis*, ©1988 House One, expurgated version.

Brochure entitled "Nipple Enlargement System" by Joel Kaplan, Ph.D., 1993.

Article entitled "The Ilizarov Technique: A Method To Regenerated Bone And Soft Tissue" by Dror Paley, M.D., et al., pp. 1–41.

Article entitled "The Callotasis Method of Limb Lengthening" by Roberto Aldegheri, M.D., et al., from *Clinical Orthopaedics and Related Research*, No. 241, Apr. 1989, pp. 137–145.

Article entitled "Histophathology of Human Expanded Tissue" by Krystyna A. Pasyk, M.D. et al., from *Clinics in Plastic Surgery*, vol. 14, No. 3, Jul. 1987, pp. 435–445.

Article entitled "The Expansion of an Area of Skin by Progressive Distention of a Subcutaneous Balloon—Use of the Method for Securing Skin for Subtotal Reconstruction of the Ear", by Charles G. Neumann, M.D. from *Plastic And Reconstructive Surgery*, Feb. 1957, pp. 124–130.

Article entitled "Tissue Expansion in Soft–Tissue Reconstruction" by Chedomir Radovan, M.D., from *Plastic and Reconstructive Surgery*, Oct. 1984, pp. 482–492.

Article entitled "Elongation of Peripheral Nerve and Viscera Containing Smooth Muscle" by Ernest K. Manders, M.D., et al., from *Clinics in Plastic Surgery*, vol. 14, No. 3, Jul. 1987, pp. 551–562.

*Microvascular Anastomoses Utilizing New Intravascular Stents* by Moskovitz et al., Ann Plast Surg, vol. 32, pp. 612–618, 1994.

*Sutureless Vasovasostomy: New Technique Using Experimental Microclip in Rat Model* by Gaskill et al., Urology, vol. 40, No. 2, 191–4, 1992.

*A New Method for Microvascular Anastomosis: Report of Experimental and Clinical Research* by Kirsch et al., The American Surgeon, vol. 12, No. 58, pp. 722–727, 1992.

*Experimental Study on Microvascular Anastomosis Using a Dissolvable Stent Support in the Lumen* by Cong et al., Microsurgery, vol. 12, p. 67–71, 1991.

*Microvascular Anastomosis Using Polyethylene Glycol 4000 and Fibrin Glue* by Kaiji et al., British Journal of Plastic Surgery, vol. 42, pp. 54–58, 1989.

*The Temporary Stent Technique: An Easier Method of Micro–Venous Anastomosis* by Wei et al., British Journal of Plastic Surgery, vol. 35, pp. 92–95, 1982.

Article entitled "Rapid Elongation of Arteries and Veins in Rats with a Tissue Expander" by G. Björn Stark, M.D., et al., from *Plastic And Reconstructive Surgery*, Oct. 1987, pp. 570–581.

Lorber, M. and Milobsky, S. Stretching of the Skin in vivo. A Method of Influencing Cell Division and Migration in the Rat Epidermis. The Journal of Investigative Dermatology 51:395, 1968.

Scheck, M. Translation of The Classic by Julius Wolff: Concerning the Interrelationship Between Form and Function of the Individual Parts of the Organism. Clinical Orthopaedics and Related Research 228:2, 1988.

Stark, G.B., Doer, A., Walgenbach, K.J., Grunwald, F., and Jaeger K. The creation of a small bowel pouch by tissue expansion—an experimental study in pigs. Langenbecks Archiv for Chirurgie 375:145, 1990.

Versaci, A.D. Reconstruction of a Pendulous Breast Utilizing a Tissue Expander. Clinics in Plastic Surgery 14:499, 1987.

Didcott, C.C. and Schnaid, E. Treatment of flexion contractures of the knee joint with a slow continuous stretch apparatus. South African Journal of Surgery 26:173, 1988.

Hodgkinson, P.D. The Use of Skeletal Traction to Correct the Flexed Pip Joint in Dupuytren's Disease. Journal of Hand Surgery 19B:534, 1994.

Aldegheri, R., Renzi–Brivio, L., and Agostini, S. The Callotasis Method of Limb Lengthening. Clinical Orthopaedics and Related Research 241:137, 1989.

Rosen, H.M. Facial Skeletal Expansion: Treatment Strategies and Rationale. Plastic and Reconstructive Surgery 89:798, 1992.

Chamay, A. and Tschantz, P. Mechanical Influences In Bone Remodeling. Experimental Research On Wolff's Law Journal of Biomechanics 5:173, 1972.

Bolinder et. al, Study of Acute Effects of Insulin–like Growth Factor I and II in Human Fat Cells, Journal of Clinical Endocrinology and Metabolism, vol. 65, pp. 732–737, 1987.

Kaplan, Ph.D., Joel Brochure entitled "Nipple Enlargement System" 1993.

Smith et al., Insulin–Like Growth Factor–I Is an Essential Regulator of the Differentiation of 3T3–L1 Apidocytes, The Journal of Biological Chemistry, vol. 263, No. 19, pp. 9402–9408, Jul. 5, 1988.

METHOD AND APPARATUS FOR EXPANDING SOFT TISSUE WITH SHAPE MEMORY ALLOYS

BACKGROUND AND SUMMARY OF THE INVENTION

It is well accepted by scientific authorities that living tissue can be made to grow in response to a gentle, sustained tensile force which, in the prior art, has generally been induced through a mechanical arrangement. This phenomenon has been demonstrated in many kinds of living tissues including skin, bone, muscle, nerves, blood vessels, lungs and even in isolated tissue cultures. (See references attached in Exhibit A.) The physiological mechanisms which contribute to this universal property of living tissue have recently been reviewed. (See references attached in Exhibit A.) Furthermore, many useful medical devices have been developed which rely on this universal property of tensile force induced tissue growth. (See references attached in Exhibit A.) However, as mentioned, these prior art devices typically operate through a mechanically induced tensile force occasioned by hooks, pins, or other more invasive, complication prone surgical procedures for establishing mechanical procedures for establishing mechanical connections between which the tensile forces are created.

The inventor herein has himself previously invented a non-invasive, mechanical device for applying a sustained tensile force to a soft tissue or skin surface to thereby enlarge a patient's soft tissue. The inventor has received patents on these various non-invasive devices and methods including U.S. Pat. Nos. 5,695,445 and 5,662,583, the disclosures of which are incorporated herein by reference. While the inventor's work is continuing, he has engaged in rigorous clinical testing as a necessary predicate to receiving FDA approval which has confirmed the clinical effectiveness of his devices and methods in enlarging soft tissue including female breasts. More particularly, the device used in his clinical studies utilizes a low level vacuum to apply a tensile force on the skin surface of a breast, with an adhesive surface being used to seal the vacuum against the patient's skin. This device takes the form of a bra-like appliance which is portable and aesthetically acceptable in that its presence is virtually undetectable as it is worn by the patient during her daily activities. These prototype devices being used are fully operational and have confirmed the effectiveness of a sustained tensile force in achieving soft tissue growth and enlargement.

As the inventor has continued his further work and development in this area, he has continued to seek ways to improve his devices with respect to their effectiveness, aesthetics, and comfort to a potential patient. One of the more difficult problems to solve with the inventor's vacuum based devices has been the need to maintain the vacuum as the device is worn throughout daily activities and yet be so unobtrusive as to be undetectable to those around the patient and who may be in close proximity to her. The inventor has developed one such device in which a vacuum may be established as the patient begins her day, and then supplemented or even reestablished with a hand operated pump and valve mechanism should the vacuum become reduced to an unacceptable level or otherwise escape as the patient twists and bends her torso in her normal daily activities. However, even with this particular arrangement, the inventor has sought to further improve his device by developing an alternative means for delivering a distracting force and yet permitting the patient to twist and turn her torso as needed without the inconvenience of reestablishing or supplementing the vacuum needed to achieve the soft tissue enlargement. While the inventor had previously conceived of various mechanical arrangements for establishing and maintaining a tensile force in this application, and indeed received U.S. Pat. No. 5,662,583 issued Sep. 2, 1997 for several of them, these arrangements were subject to their own difficulties. For example, several of them required a somewhat elaborate arrangement of mechanical springs, wires, interleaved shell members, or other such mechanical and moving parts as to be fairly intricate and perhaps difficult to reliably implement. Another embodiment disclosed and claimed in the '583 patent included utilizing an intermediate material which could be caused to shrink upon curing. While such a curably shrinking material could effectively create the desired tensile force, it would necessarily require replacement of the once shrunk intermediate material at least on a daily basis as the patient would remove the bra and then reapply it. For these reasons, among others, the inventor has previously focused his activities on vacuum based devices.

In order to solve the potential difficulties with maintaining a vacuum in the vacuum based devices and the intricacies of the mechanical devices, the inventor herein has succeeded in conceiving and developing a further mechanical embodiment for creating the required tensile force in a soft tissue expander. More particularly, the inventor has conceived of utilizing a "memory material" which may be moved into a first physical arrangement for being adhered to the surface of the soft tissue desired to be enlarged, and then causing the memory material to transform into its second physical arrangement to thereby create the required tensile force. The first physical arrangement may be a non-memory arrangement and the second physical arrangement may be the memory arrangement. More particularly, the memory material may comprise one of the shape memory alloys, an example of which is Nitinol as disclosed in U.S. Pat. No. 3,174,851, the disclosure of which is incorporated herein by reference. Nitinol and some other related nickel-titanium or copper-zinc-aluminum methyl alloys have a "shape memory affect" that has been previously utilized in a number of useful medical devices. These include as an orthodontic arch where the arch is cooled and then placed in the patient's mouth which warms it and moves it into a stressed shape to exert pressure on the patient's teeth. Still other medical applications known to the inventor are as an expandable filter which is used in the blood vessels and as a bony anchor. These shape memory alloys or "SMA" have two crystalline phase forms with a transition temperature that can be set at approximately normal body surface temperature (approximately 30 degrees centigrade). At temperatures greater than this transition temperature, these alloys prefer the Austenite phase while at lower temperatures they prefer the Martensite phase. The Martensite phase crystal structure consists of a series of planes that may be readily displaced allowing the alloy to be easily deformed in nearly any direction. When the alloys are heated to a temperature at or above the transition temperature, the Austenite crystal phase is preferred which forces the planes to revert back into their original configuration. In effect, this hardens the alloys and forces them to spring back and restore their original or "set" shape. These alloys may also be activated by passing an electrical current through them. Thus, these metal alloys give the appearance of "remembering" their originally set shape. Cooling and heating these alloys below and above the transition temperature can be repeated thousands of times, each time changing the property of the alloy from being soft for fashioning into a second physical arrangement to rigid which causes them to spring back into their set shape or original physical arrangement. the set shape or "shape memory" may be set by imprinting the desired form or shape into the alloy and then heating it to temperatures approximating 500 degrees centigrade.

In addition to shape memory alloys, certain plastics may also be engineered to move between a first physical arrangement and a second physical arrangement as a function of temperature, as known to those of ordinary skill in the art. These plastics may also be utilized as a "memory material" suitable for implementing the present invention.

In implementing these memory materials, the cups or domes described in one or more of the inventor's previous patents could include some form of memory material in their fabric. Below body temperature, these domes would be soft and conformable to the shape and contour of the underlying breast or soft tissue surface to be enlarged. As the patient's body temperature heats the domes and memory material, they will tend to revert and spring back to their previously imprinted "memory" of a deeper/wider dome. If appropriately adhered to the underlying soft tissue surface or skin, this reversion or "springing back" of the memory material will then impart a tensile force to the underlying skin or tissue surface as would be effective for creating soft tissue enlargement in a suitable therapeutic regimen. Additionally, a small battery operated electronic circuit may be provided to activate and increase the tension of some of the fibers that would be set for a higher transition temperature. This would allow the bra to operate in an intermittent duty cycle in addition to maintaining a constant tension.

In order to appropriately distribute the tensile force while at the same time adhering the memory material to the underlying tissue, a layer of gel, or an air or other fluid filled bladder, may be an appropriate interface between the skin and layer of memory material, and an appropriate adhesive substance placed between the layer of gel and the underlying skin. As the inventor has disclosed in one or more of his prior patents, this adhesion could be effected with any one of a well known group of surgical adhesives which are known to bond appropriately to a skin surface without damage for extended periods of time. This may preferably be a layer of sticky silicone gel. Alternatively, the inventor has further conceived of implementing the principles of surface tension as a non-abrasive way of achieving this necessary adhesion. More particularly, a fluid may be placed on the gel layer, or on the patient's soft tissue just prior to application of the bra, and the inventor has found that the forces attributable to surface tension are sufficient to maintain an appropriate adherence between the soft tissue and the gel as the memory material transitions physical arrangement to thereby impart the desired tensile force. Thus, the inventor has conceived of utilizing a memory material for mechanically inducing a tensile force in an appropriately chosen soft tissue site, as well as the concept of utilizing a thin layer of fluid as an interface for creating a surface tension to maintain adherence between a layer of gel or other intermediary layer to insure a distribution of the tensile force across the skin surface to thereby avoid undesired shear forces or other concentrating effects which might cause undesired abrasion or damage to the skin surface.

While some of the principal advantages and features of the invention have been discussed above, a fuller understanding of the invention may be attained by referring to the drawings and description of the preferred embodiment which follow.

DETAILED DESCRIPTION OF THE PREFERRED EMBODIMENTS

Figure 1:
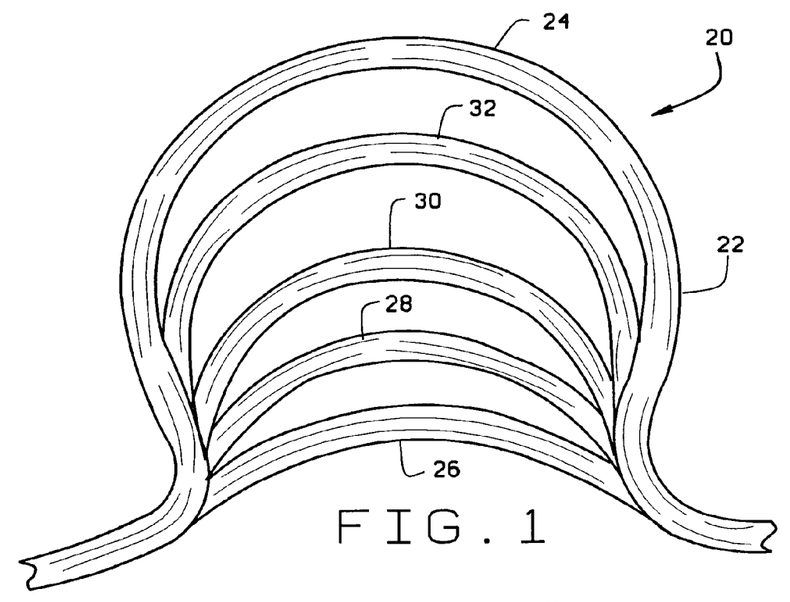
FIG. 1 depicts in cross section the successive positions of a memory material as it transitions from a first physical arrangement to a second physical arrangement.

As shown in FIG. 1, a dome 20 of memory material 22 may be treated to "set" its shape in a memory as depicted in position 24. As used in the present invention, the memory material 20 may be chosen to be a shape memory alloy having a transition temperature at approximately body surface temperature which is approximately 30 degrees centigrade. As the shape memory alloy is taken to a lower temperature, it may then be fashioned into a shape such as that shown at position 26. Then, as the temperature of the memory material approaches its transition temperature, it may successively taken on the shape shown at positions 28, 30, 32, and then reaching its memory position at position 24. Thus, a memory material may be used in the present invention to provide a bra or other dome like structure which may be fashioned into a relatively shallow shape but which upon reaching its transition temperature deflects to a significant degree in order to provide the mechanism for creating a mechanical tensile force in an underlying soft tissue.

Figure 2:
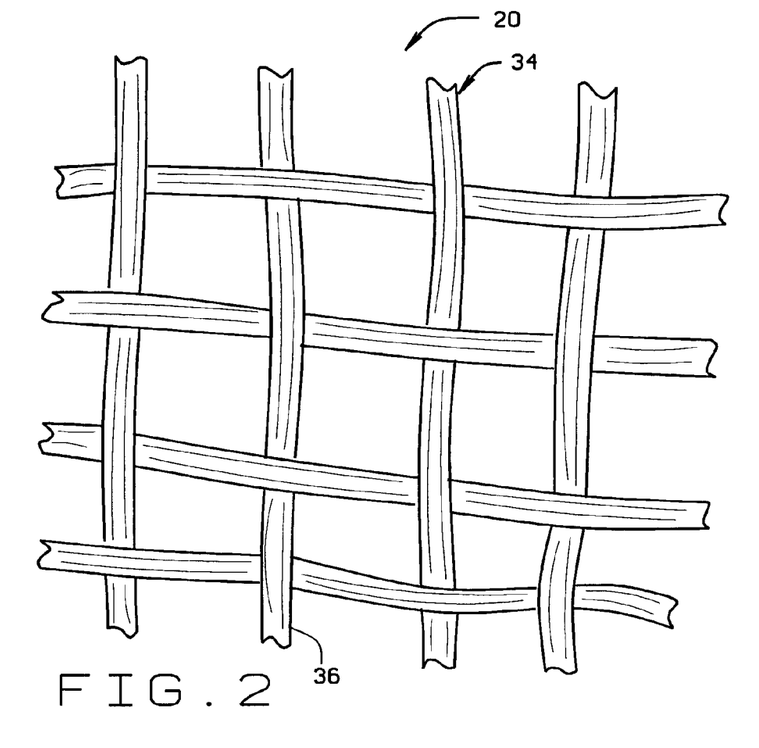
FIG. 2 is an enlargement of a weave formed from a plurality of complex fibers woven into a weave of memory material.

Referring now to FIG. 2, the memory material 20 as used in the bra embodiment of the present invention, may be fashioned from a weave 34 comprised of a mesh or cross pattern of a plurality of individual complex fibers 36. Each complex fiber 36 may be a coil, spring, or serpentine arrangement of one or more strands of a shape memory alloy or, alternately, thin strips of shape memory alloy may be interweaved together and, by being able to glide past each other provide the necessary allowance for expansion and contraction of the material as it transitions between a first physical arrangement and a second physical arrangement. Although these constructions of the memory material are considered as preferable by the inventor in implementing his present invention, as known to those of ordinary skill in the art still other constructions may be used in implementing the memory material, it only being required that its construction be amenable to allow for the desired excursion between the two physical arrangements as desired to effect a tensile force in an underlying soft tissue.

Figure 3A:
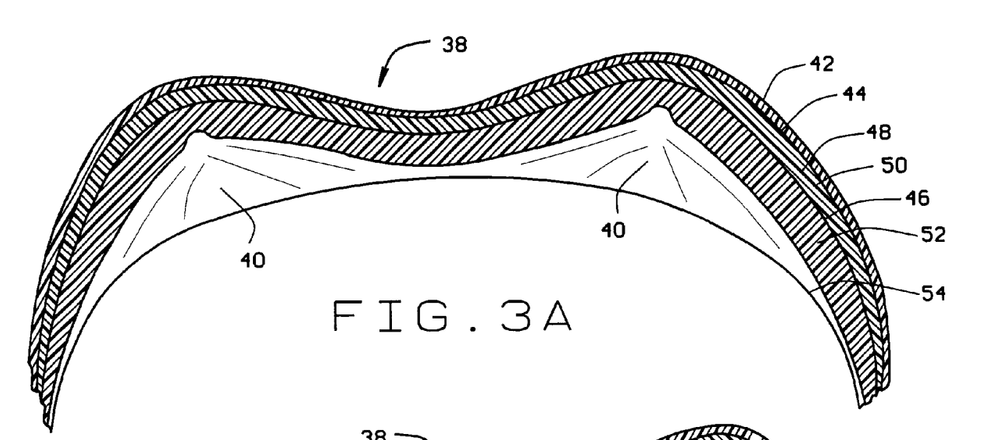
FIGS. 3a & b are cross sectional views of a bra incorporating the present invention with FIG. 3a depicting the bra configured as the memory material is in a first physical arrangement and FIG. 3b depicting the bra configuration as the memory material has transitioned into a second physical arrangement.
Figure 3B:
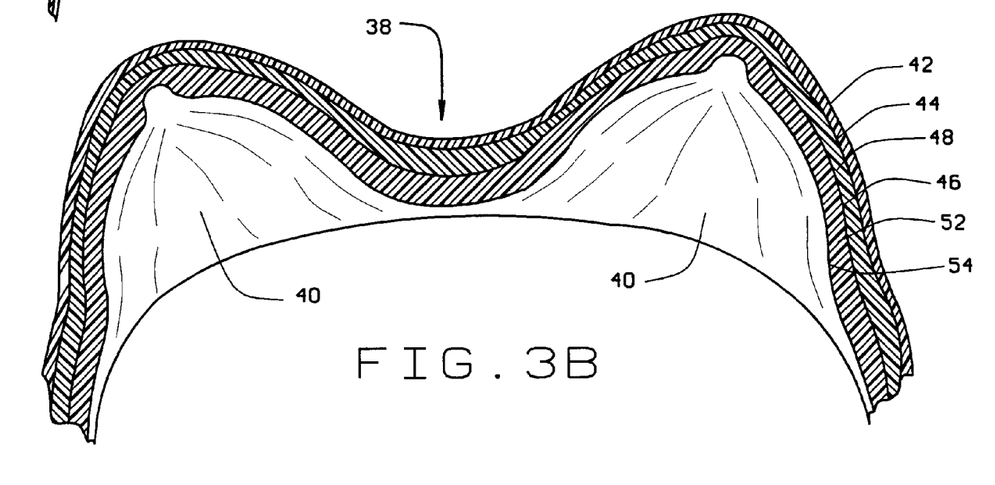
Figure 4:
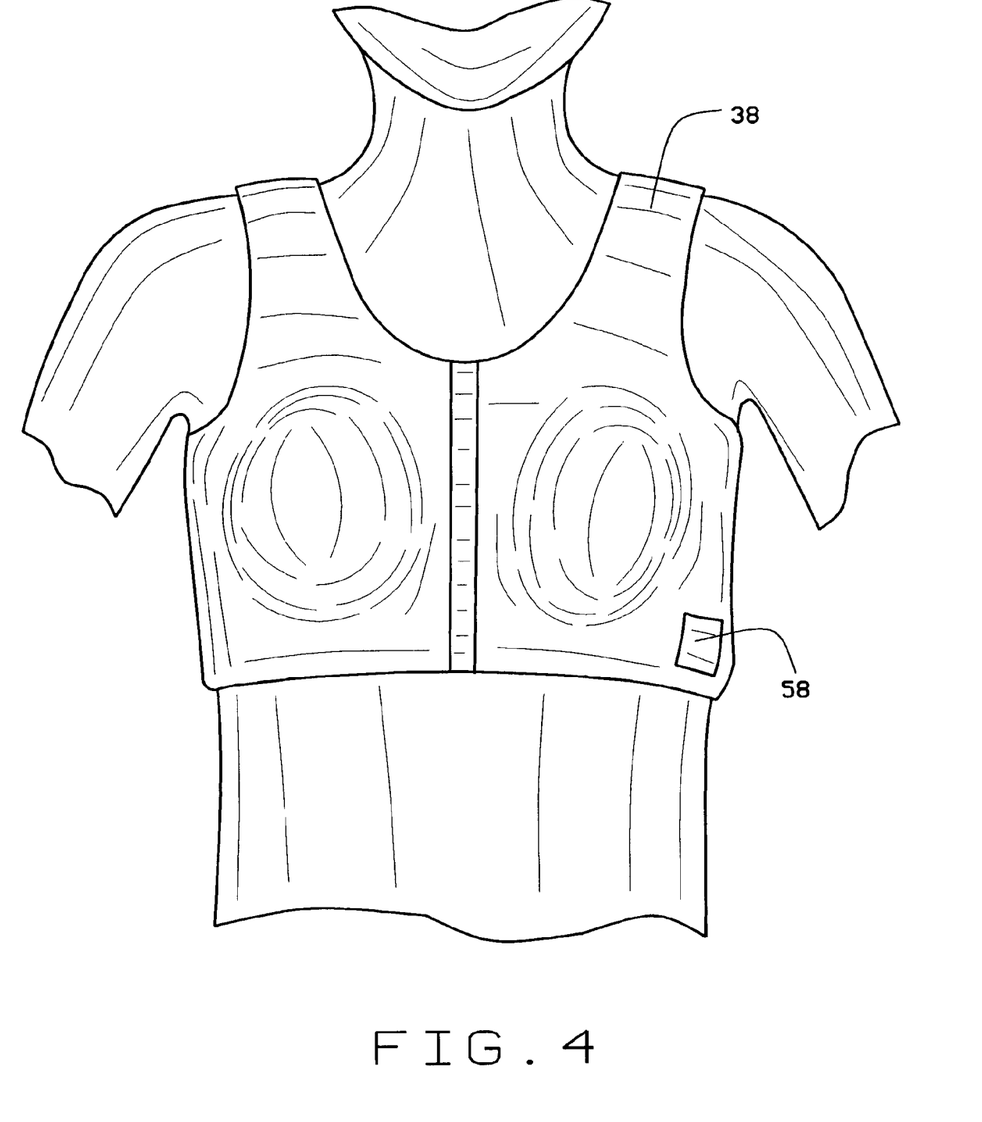
FIG. 4 depicts a frontal view of a patient wearing the bra embodiment of the invention.

As shown in FIGS. 3a and b, a bra 38 constructed in accordance with the teachings of the present invention provides a good application for enlarging a patient's soft tissue such as a pair of female breasts 40. As shown therein, the bra 38 comprises a multi-layer construction. An outer layer 42 may be a supportive bra having an ornamental, aesthetic, or decorative covering as may be pleasing to the feminine eye. Beneath is preferably an outer layer of expandable or extensible material 44 which, with a corresponding similar layer 46, surrounds therebetween a layer 48 of memory material for imposing a tensile force as it is caused to move from the first physical arrangement as shown in FIG. 3a to the second physical arrangement as shown as FIG. 3b. The memory material 48 may be bathed by a lubricating fluid or gel 50 to facilitate the multiple cycling of the memory material between its two physical arrangements. A fluid layer, which may comprise a layer of gel 52 or an air or fluid filled bladder or other such spacer, may preferably then be provided to help conform the bra 38 to the body contour and to prevent pressure points and shear forces between the bra 38 and the underlying soft tissue 40. The fluid layer 52 may be confined itself inside an extensible envelope similar to the layers of extensible material 44, 46. Lastly, on the inside surface of the fluid layer 52, a layer of adhesive 54 may be applied to adhere the fluid layer 52 to the skin of the soft tissue 40 and to avoid any separation therebetween as the bra 38 is cycled between the positions shown in FIGS. 3a and b. Alternatively, a fluid may be provided instead of an adhesive layer with the adhesive forces thus being provided by surface tension. Indeed, the inventor contemplates that it may be preferable for a thin film of fluid to be provided as it is thought to be less susceptible to shear forces and therefore less likely to abrade the skin surface upon repeated use of the bra 38 over any extended period of time as might be recommended in a typical therapeutic regimen. As contemplated by the inventor, the bra 38 of the present embodiment of the invention, as worn by a patient, is shown in FIG. 4.

Figure 5:
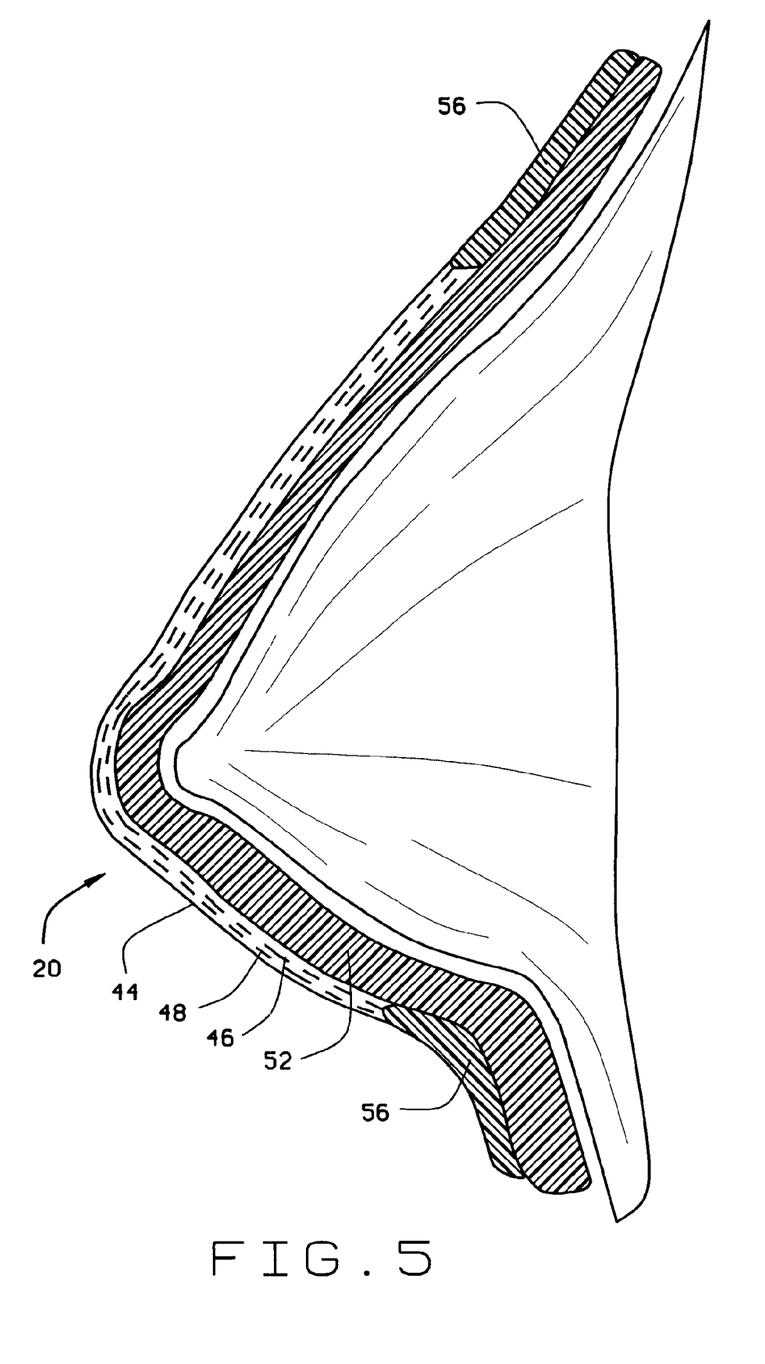
FIG. 5 is a cross sectional view detailing the bra embodiment of the invention as adhered to a breast.

As is taught in several of his prior patents, the inventor contemplates that a ring, periphery, or lip 56, as best shown in FIG. 5, may be integrally formed as part of the dome 20, and surround it at its periphery, to support it against the patient's chest as the offsetting surface for the compressive force which balances the tensile force created by the bra 20. With this supporting ring 56, the domes 20 may be supported from the patient and thereby have their forces balanced to achieve an effective tensile force in the soft tissue as is required to achieve the purposes of the invention. For a more detailed explanation, reference is made to any one or more of the inventor's prior patents mentioned above. However, it should be noted that with the present invention, the ring or periphery 56 may be either integrally formed with the dome 20 or constructed from material which does not exhibit the "memory" feature as is used to form the arcuate portion of the dome 20. Instead, any suitable structural material may be used with the memory material spanning the interior of the ring 56. With either embodiment, the inventor contemplates that a dome 20 could readily be constructed which would expand between two to three times its periphery which would correlate to a five times to ten times increase in surface area of the dome 20. With this degree of excursion, a substantial tensile force could be created although, as is known to those of ordinary skill in the art, lesser forces and smaller excursions could readily be provided for using the teachings herein as well as the known information relating to shape memory alloys and other types of memory materials.

For implementation as a breast enlargement device, such as with the bra embodiment of the invention as is explained in some detail herein, a bra could readily be constructed of a soft forming material at temperatures below body surface temperature, with the cup areas of the bra containing shape memory alloy fibers, weave, mesh, or sheets in its fabric. The bra would first have its memory material "set" in an appropriate shape, as predetermined to direct the growth in the chosen locations of the patient's breast by properly applying the desired tensile force. In other words, with the bra of the present invention, the breast may be contoured and sculpted by encouraging growth in preselected areas to thereby fill in where needed. The bra is then placed on a patient, with appropriate attention being given to properly adhere the bra interior lining or gel to the skin of the breast by applying either a layer of fluid or adhesive. The bra cups are heated by the natural heat of the patient's breasts to approach the body surface temperature which is approximately thirty degrees centigrade. As the temperature of the bra rises, the shape memory alloy acts as a spring and as it returns to its "memory" configuration it exerts a tensile force on the patient's breasts, pulling the breasts along with them as they reconfigure into a deeper dome shape. With appropriate engineering design as would be known of those of ordinary skill in the art, the tensile force of the alloy spring weave/sheet can be appropriately adjusted to exert an evenly applied, or shaped uneven force to provide for sculpting of the breast, distending or distracting force substantially equal to the approximately 15 to 30 mmHg of pressure as taught with the inventor's prior vacuum type bra devices. Alternately, a greater or lesser tensile force could be engineered as desired depending upon the appropriate therapeutic regimen recommended, or as learned to be more physiologically effective through greater clinical experience with the bra of the present invention. Additionally, several of the fibers may be set at a higher transition temperature and then activated by a battery powered electronic circuit 58 to cycle intermittently to thereby provide a supplemental tensile force, as desired. The battery powered electronic circuit 58 may be appropriately concealed at any convenient point on the bra, and connected to those fibers selected to be in the region of interest to apply the force in the manner and location desired. Further refinement of the construction and design using finite element analysis, as would be well known to those of ordinary skill in the art, can maintain this tensile force constant as the spring like reversion pulls from a flat sheet to a spherical structure having a depth even greater than a hemisphere.

While the embodiment best explained herein relates to the use of a bra to expand the female breast, it would be apparent to those of ordinary skill in the art that the present invention may also be used in other applications without undue experimentation. Examples of these include as a simple soft tissue expander as might be useful for replacing collagen and fat injections and other aloplastic implants typically used in the prior art to improve contour defects caused by aging, involution or scarring. With an appropriately designed mask to be worn at night, for example, wrinkles, dimples, lips and even sunken or hollowed features of the face may be filled by expanded soft tissue whose growth would be induced by the present invention. For such applications, the dome and surrounding lip or periphery would be used.

It should also be apparent to those of ordinary skill in the art that the particular fluid utilized to create the surface tension for achieving adherence between the fluid layer or other liner surface may be chosen from amongst many suitable fluids including mineral oil, baby oil, water, physiologic saline, various kinds of water or oil based gels, glycerine, creams, and ointments, all of which have been found to adhere to the skin surface and withstand tensile forces in excess of the approximate 15 to 30 mmHg required in various therapeutic regimens with the vacuum based device. In several of those embodiments, a thin membrane is bonded to the skin and the vacuum is generated in the enclosed space between the inner surface of the membrane and the dome. In this embodiment, surface tension has been successfully implemented by the inventor. Furthermore, it is believed that the thin membrane embodiment may also be successfully implemented in the memory material embodiment as disclosed and claimed herein.

Various changes and modifications to the invention would be apparent to those of ordinary skill in the art. Those changes, variations, and modifications are fairly included in the scope of the present invention which should be considered as limited by only by the scope of the claims appended hereto and their legal equivalents.

What is claimed is:

1. A device for expanding a patient's soft tissue, said device comprising a dome adapted for placement in a sealing condition over a soft tissue site desired to be enlarged, said dome comprising a layer of memory material;
   a sticky layer extending across an interior of said dome for providing the sealing condition of said dome to said soft tissue site; and
   a fluid layer located between the layer of memory material and said sticky layer, said fluid layer minimizing any lateral stress force between the layer of memory material and said soft tissue.

2. The device of claim 1 further comprising a liner, said liner being secured inside of said layer of memory material, said liner being adapted to provide a surface for said sticky layer, said sticky layer being provided by surface tension.

3. The device of claim 1 wherein said sticky layer comprises a layer of adhesive material.

4. A device for expanding a patient's soft tissue, said device comprising a dome adapted for placement in a sealing condition over a soft tissue site desired to be enlarged, said dome comprising a layer of memory material;
   a sticky layer extending across an interior of said dome for providing the sealing condition of said dome to said soft tissue site; and
   said memory material comprises a shape memory alloy, said shape memory alloy having a transition temperature set at about normal human body surface temperature.

5. A device for expanding a patient's soft tissue, said device comprising a dome adapted for placement in a sealing condition over a soft tissue site desired to be enlarged, said dome comprising a layer of memory material;
   a sticky layer extending across an interior of said dome for providing the sealing condition of said dome to said soft tissue site; and
   said layer of memory material comprises a weave of memory material.

6. The device of claim 5 wherein said weave of memory material is formed of a plurality of individual fibers of said memory material, each of said fibers comprising a complex fiber.

7. The device of claim 6 further comprising an electronic circuit, and wherein a selected number of said fibers are electrically connected to said electronic circuit to permit their separate transition from one physical arrangement to another.

8. The device of claim 5 wherein said weave of memory material is formed of a plurality of relatively thin strips of said memory material.

9. The device of claim 5 further comprising a ring positioned generally about a periphery of said dome, said weave of memory material extending across said ring and said ring defining the soft tissue site to be enlarged when sealed to said patient's soft tissue.

10. The device of claim 9 wherein said ring is integrally formed as part of said dome.

11. The device of claim 10 wherein said ring is made of material other than memory material.

12. A device for expanding a patient's soft tissue, said device comprising a dome adapted for placement in a sealing condition over a soft tissue site desired to be enlarged, said dome comprising a layer of memory material;
    wherein said device is in the form of a bra for enlarging a patient's breast size; and further comprising:
      a sticky layer extending across an interior of said at least one dome providing the sealing condition of said at least one dome to said patient's breast; and
      a liner, said liner being secured inside of said layer of memory material, said liner being adapted to provide a surface for said sticky layer.

13. The bra of claim 12 wherein said layer of memory material comprises a weave of memory material.

14. The bra of claim 13 wherein said memory material comprises a shape memory alloy, said memory alloy having a transition temperature set at about normal human body surface temperature.

15. The bra of claim 13 further comprising an electronic circuit, and wherein a selected portion of said weave is electrically connected to said electronic circuit to permit its separate transition from one physical arrangement to another.

16. The bra of claim 13 further comprising a ring positioned generally about a periphery of said dome, said weave of memory material extending across said ring and said ring defining the portion of said patient's breast to be enlarged when adhered to said patient's breast.

17. The bra of claim 16 wherein said ring is integrally formed as part of said dome.

18. The bra of claim 17 further comprising a fluid layer located between the layer of memory material and said sticky layer, said fluid layer minimizing any lateral stress force between the layer of memory material and said breast.

19. The bra of claim 18 wherein said bra includes a pair of said domes.

20. The bra of claim 19 wherein said bra further comprises a surface for counterbalancing any stress forces created by said memory material.

21. The bra of claim 20 wherein said memory material is secured to said fluid layer.

22. The bra of claim 21 wherein said memory material is sandwiched between a pair of layers of expandable material.

23. The bra of claim 22 wherein said memory material comprises a shape memory alloy, said memory alloy having a transition temperature set at about normal human body surface temperature.

24. A device for expanding a patient's soft tissue, said device comprising a dome adapted for placement in a sealing condition over a soft tissue site desired to be enlarged, said dome comprising a layer of memory material;
    wherein said device is in the form of a bra for enlarging a patient's breast size; and further comprising:
      a sticky layer extending across an interior of said at least one dome providing the sealing condition of said at least one dome to said patient's breast; and
      further comprising a fluid layer located between the layer of memory material and said sticky layer, said fluid layer minimizing any lateral stress force between the layer of memory material and said breast.

25. A device for expanding a patient's soft tissue, said device comprising a dome adapted for placement in a sealing condition over a soft tissue site desired to be enlarged, said dome comprising a layer of memory material;

wherein said device is in the form of a bra for enlarging the breast size of a patient, said bra includes a pair of domes for fitting to a pair of said patient's breasts where each of said domes is made of a shape memory alloy weave woven of complex fibers, a fluid layer adhered to an inside surface of each of said domes, and an adhesive layer applied to an inside layer of each of said fluid layers so that each of said domes may be adhered to one of said breasts as said shape memory alloy is in a first physical configuration and which will exert a tensional force on each of said breasts as said shape memory alloy returns to an original configuration.

26. The bra of claim 25 wherein said adhesive layer comprises a layer of an adhesive.

27. The bra of claim 25 wherein said adhesive layer comprises a layer of moisture sufficient to create an adhesive force with surface tension.

* * * * *